United States Patent [19]

Miller et al.

[11] Patent Number: 4,917,102

[45] Date of Patent: Apr. 17, 1990

[54] GUIDEWIRE ASSEMBLY WITH STEERABLE ADJUSTABLE TIP

[75] Inventors: Gary H. Miller, Milpitas; Jeffrey L. Kraus, San Jose; Linda T. Guthrie, Fremont, all of Calif.

[73] Assignee: Advanced Cardiovascular Systems, Inc., Santa Clara, Calif.

[21] Appl. No.: 244,817

[22] Filed: Sep. 14, 1988

[51] Int. Cl.⁴ .............................................. A61B 5/00
[52] U.S. Cl. ................................... 128/772; 128/657; 604/164; 606/194
[58] Field of Search ................. 604/93, 95, 170, 287, 604/164; 128/772, 656–658, 344

[56] References Cited

U.S. PATENT DOCUMENTS

| | | |
|---|---|---|
| 2,024,982 | 12/1935 | Scott . |
| 3,452,740 | 7/1969 | Muller . |
| 3,452,742 | 7/1969 | Muller . |
| 3,521,620 | 7/1970 | Cook . |
| 3,528,406 | 9/1970 | Jeckel et al. . |
| 3,547,103 | 12/1970 | Cook . |
| 3,552,384 | 1/1971 | Pierce . |
| 3,749,086 | 7/1973 | Kline et al. . |
| 4,033,331 | 7/1977 | Guss et al. . |
| 4,215,703 | 8/1980 | Willson . |
| 4,456,017 | 6/1984 | Miles . |
| 4,498,482 | 2/1985 | Williams . |
| 4,548,206 | 10/1985 | Osborne . |
| 4,676,249 | 6/1987 | Arennes et al. . |
| 4,719,924 | 1/1988 | Crittenden et al. . |
| 4,779,628 | 10/1988 | Machek ............................... 128/772 |

*Primary Examiner*—Stephen C. Pellegrino
*Attorney, Agent, or Firm*—Fulwider, Patton, Lee & Utecht

[57] ABSTRACT

A guidewire assembly particularly suitable for valvuloplasty procedures have an outer tubular member a first shapable core member fixed within the outer member and a second stiffer core member which is axially movable within the out tubular member. The first core member preferably has a double curvature shape with the most distal curvature having a much smaller radius or curvature than the second curvature. When the movable core member is moved proximally, the fixed core member assumes its shaped form and thereby changes the shape of the guidewire. The double curvature shape prevents the traumatic engagement of the distal tip of the guidewire with the lining in the heart chamber and also provides supports to the guidewire when disposed through the heart valve.

17 Claims, 2 Drawing Sheets

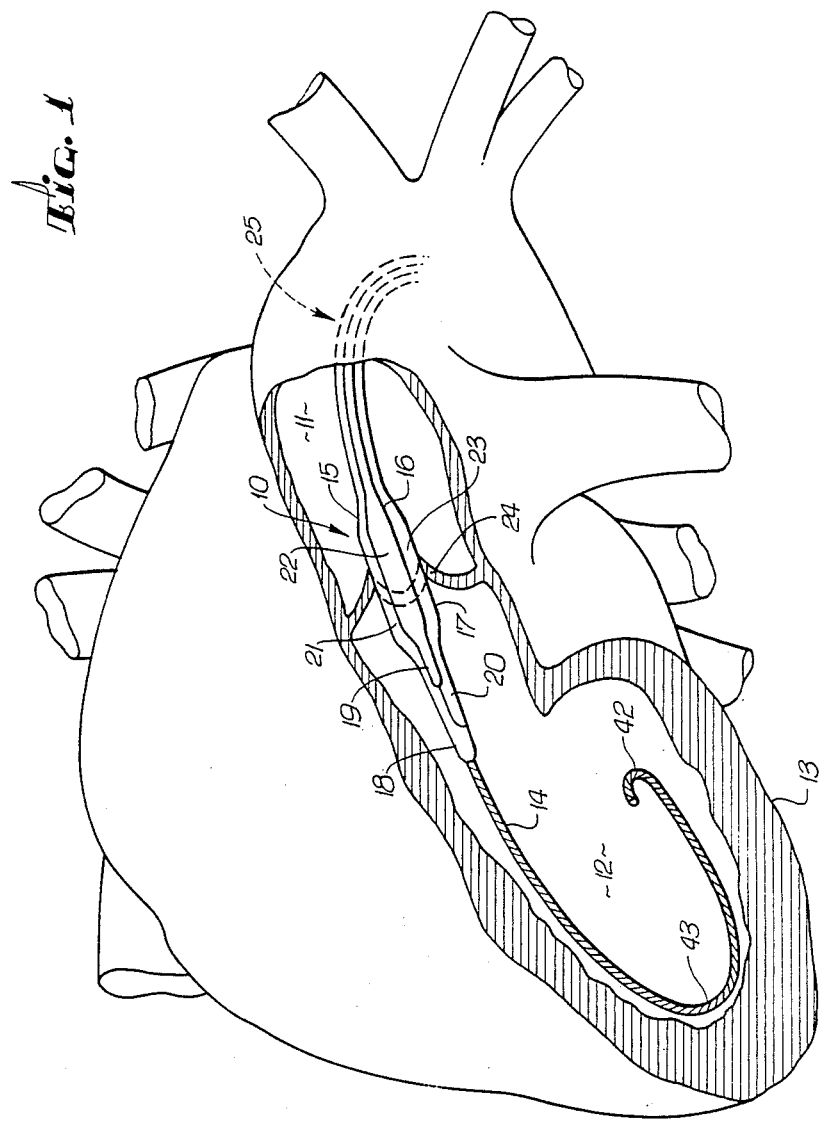

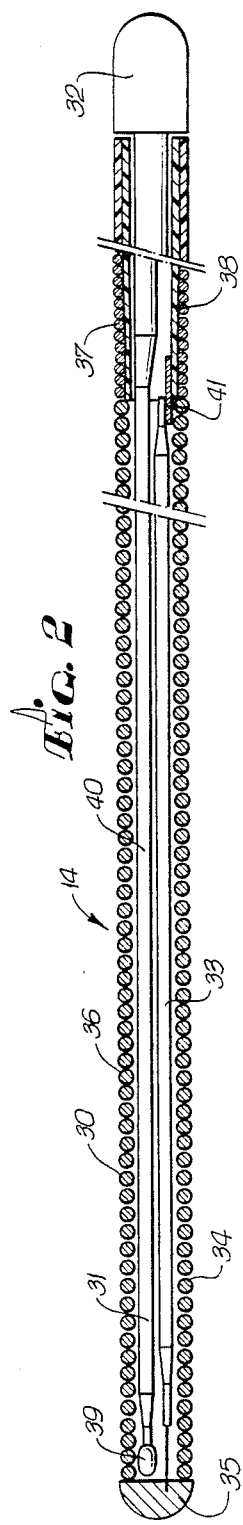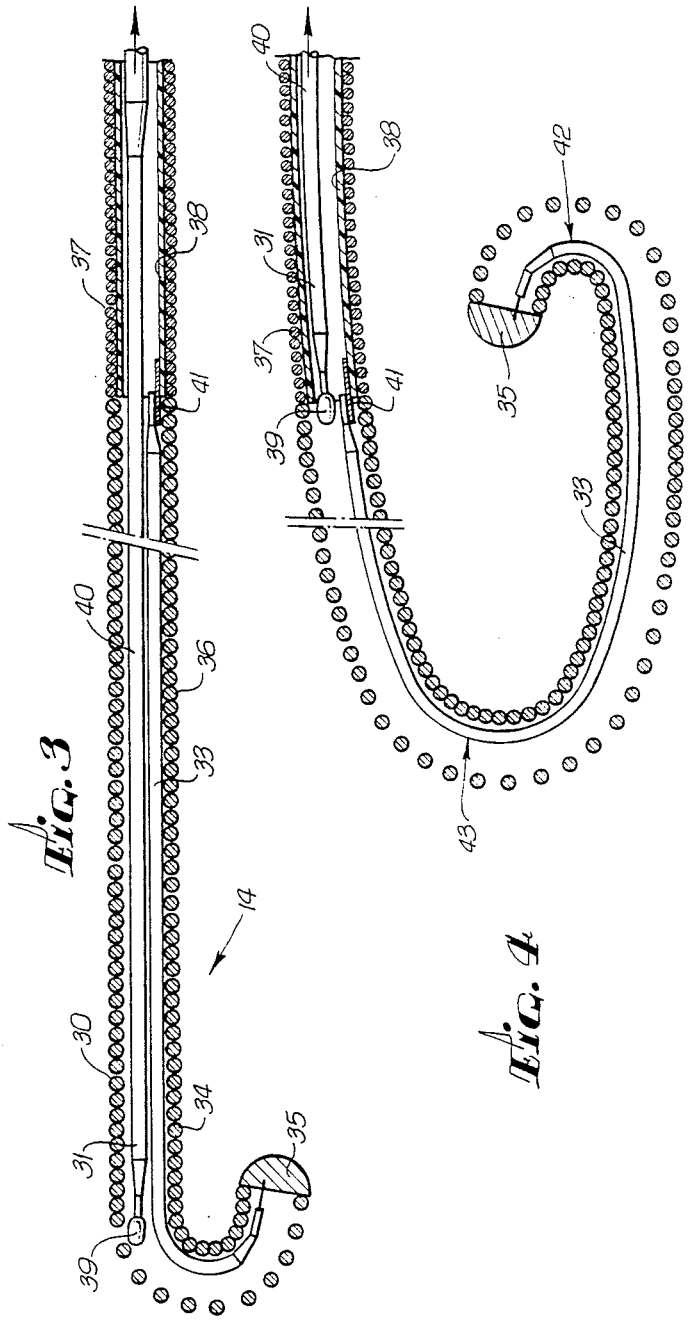

GUIDEWIRE ASSEMBLY WITH STEERABLE ADJUSTABLE TIP

BACKGROUND OF THE INVENTION

This invention pertains generally to a guidewire assembly which is particularly useful with dilatation catheters in valvuloplasty procedures.

Balloon dilatation catheters have come into widespread use for treating stenotic lesions in coronary and peripheral arteries. These catheters are typically advanced through a patient's vasculature over a guidewire assembly until the inflatable balloon on the distal extremity of the catheter traverses the stenosis to be dilated. The balloon is then inflated to dilate the opening or lumen.

Stenoses can also occur in heart valves, particularly the aortic and mitral valves. While in the past valve replacement might be the preferred treatment, particularly with severe stenoses, more frequently the valvular stenosis has been successfully treated with dilatation balloon catheters in a procedure known as valvuloplasty or commissurotomy. However, in these procedures, the inflatable balloons are much larger than those used in typical coronary and peripheral dilatations. Moreover, a plurality of balloons are frequently disposed across the stenotic valves and inflated simultaneously to effectively dilate the heart valves.

In order to advance the relatively large diameter balloon catheters across the aortic or mitral valves, a relatively stiff guidewire must be first passed through the valve. However, once the relatively stiff guidewire has passed through the valve, care must be exercised in order to ensure that the distal tip of the guidewire does not traumatically engage the inner lining of the heart.

What has been needed and heretofore unavailable is a guidewire assembly for valvuloplasty procedure, which can be relatively stiff to facilitate passage through a mitral or aortic valve but which can assume a flexible, non-traumatic form once advanced through the valve in order to avoid injury to the interior of the heart. The present invention satisfies that need.

SUMMARY OF THE INVENTION

This invention is directed to a guidewire assembly for a balloon dilatation catheter and is particularly suitable for use in valvuloplasty procedures.

The guidewire assembly in accordance with the invention generally comprises a flexible outer tubular member, a relatively stiff, movable member or core disposed within the flexible outer member, and a second relatively flexible, fixed inner member or core disposed within the flexible outer member. The movable inner core member which is relatively stiff with respect to the fixed core member extends along essentially the entire length of the guidewire and has a handle on the proximal end thereof to axially move the inner movable core within the outer tubular member. The fixed inner member is preferably shorter and considerably more flexible than the movable member and is secured within the distal extremity of the outer tubular member. The distal end of the fixed core is secured to a plug of radiopaque material provided on the distal tip of the catheter, and the proximal end thereof is secured to the outer tubular member to prevent the axial movement therein The fixed core is preshaped, preferably with a double curvature, the most distal curvature having a much smaller radius of curvature than the proximal curvature.

The movable core is generally considerably stiffer than the preshaped fixed core member so that, when the movable core is coextensive with the fixed core member within the outer tubular member, the stiffness of the first or movable core member is sufficient to overcome the curvature provided to the second or fixed core member so that the overall shape of the distal portion of the guidewire is relatively straight. This stiffness provided by the movable core member also provides improved pushability to the guidewire to aid in passing the distal portion thereof through highly stenotic valves.

However, once through a stenotic mitral or aortic valve, the movable core member is axially moved in the proximal direction by means of the handle on the proximal end thereof so that the distal end of the movable inner member is no longer coextensive with that of the fixed core member. As the movable core is moved further proximal so as to be no longer coextensive with the preshaped curved section of the fixed core member, curvature of the fixed core member then begins to control the shape of the distal end of the guidewire. The smaller more distal curve of the guidewire, when the movable member is first moved in the proximal direction, allows the guidewire to be steered through a patient's vasculature and, when further moved, prevents a direct impact of the distal tip of the guidewire with the heart lining. As the movable member is moved further proximal the distal portion of the guidewire assumes the second curvature preshaped into the fixed core member to facilitate the placement thereof against the endocardium of the ventricle. This latter position anchors and supports the guidewire within the ventricle as relatively large dilatation balloons are advanced over the guidewire through a stenotic heart valve.

These and other advantages of the invention will become more apparent from the following detailed description thereof when taken in conjunction with the following exemplary drawings.

BRIEF DESCRIPTION OF THE DRAWINGS

FIG. 1 is a schematic, cut-away anterior view of a human heart with a multiple balloon valvuloplasty catheter assembly embodying features of the invention placed across the aortic valve;

FIG. 2 is a longitudinal view in section of a guidewire shown on FIG. 1 embodying features of the invention;

FIG. 3 is a longitudinal view in section of the distal portion of the guidewire shown in FIG. 2 with internal members axially displaced to illustrate an initial curvature of the distal tip of the guidewire; and FIG. 4 is a longitudinal view in section of the distal portion of the guidewire shown in FIG. 2 with internal members axially displaced to illustrate a double curvature of the distal tip of the guidewire.

DETAILED DESCRIPTION OF THE INVENTION

FIG. 1 illustrates a multiple balloon valvuloplasty dilatation catheter-guidewire assembly 10 embodying features of the invention. As shown in FIG. 1, the assembly 10 is positioned through the left atrium 11 and into the left ventricle 12 of a human heart 13. The assembly 10 generally comprises a guidewire 14, three balloon dilatation catheters 15, 16, and 17 which have sleeves 18, 19, and 20 on the distal ends thereof which are slidably mounted onto guidewire 14. The balloons 21, 22, and 23 of catheters 15, 16, and 17, respectively, are shown traversing the aortic valve 24. The guidewire 14 and the catheters 15, 16, and 17 were percutaneously introduced into the femoral artery (not shown), advanced therethrough and through the aortic arch 25 and ultimately through the aortic valve 24 until the balloons 21, 22, and 23 are properly positioned across the valve. The guidewire 14 is first pushed through the aortic valve 24, then the individual dilatation catheters 15, 16, and 17 are advanced over the guidewire 11 through the valve. Once across stenotic arterial valve 24, the balloons 21, 22, and 23 are inflated to dilate the valve. Details of the catheter structure and the operation thereof can be found in copending application, Ser. No. 199,940, filed May 27, 1988, entitled Vascular Catheter Assembly With A Guiding Sleeve, which is incorporated herein by reference.

FIG. 2 illustrates details of the guidewire 14 which embodies features of the invention. As shown, the guidewire 14 generally comprises an flexible, outer tubular member 30, a relatively rigid inner movable core 31 which extends along essentially the entire interior of the outer tubular member 30 and which has a handle 32 on the proximal end thereof to axially move the movable core 31 within the outer tubular member 30, and a relatively flexible inner core member 33 which is fixed within the interior of the outer tubular member 30. The movable core 31 and the fixed core 33 can be formed of suitable material such as stainless steel or nitinol.

The outer tubular member 30, as shown in FIG. 2, generally comprises a helical coil 34 extending proximally from plug 35 at the distal tip of the guidewire 14. The distal coil section 36 of helical coil 34 is preferably formed of radiopaque material such as titanium, platinum, and alloys thereof which facilitate the fluoroscopic observation of the distal portion during valvuloplasty procedures and yet provide suitable mechanical properties for the intended use. The proximal end of distal coil section 36 is threaded into the distal end of proximal coil section 37 which is preferably formed of stainless steel and the threaded sections ar joined together by suitable means such as welding, brazing, soldering, and the like. The proximal coil section 37 is preferably supported along its length by a tubular member 38 which extends proximally to the proximal extremity of guidewire 14. Preferably, all or a substantial portion of the supporting tube 38 is plastic tubing such as polyimide tubing.

The fixed core 33 is secured by its distal tip to plug 35 and the proximal end thereof is secured by suitable means such as welding, soldering brazing and the like to a short section of hypotube 41 which is in turn joined to tubular support member 38 by a suitable adhesive such as a Loktite 405.

The movable core 31 has a handle 32 which is secured to the distal end to facilitate the axial movement of the movable core. The distal tip 39 of the movable core 31 extends into the distal extremity of the guidewire 14 but is not secured to the plug 35 or to the outer tubular member 30. The tip 39 may be rounded, as shown, to prevent passage through the coil sections 36 and 37. Additionally, the movable core may be provided with a collar (not shown) which extends about the fixed core 33.

The tapered distal portion 40 of the movable core 31 is much more stiff than the fixed core 33 so that, when the fixed core is shaped, the stiffness of the distal portion 40 of the movable core will prevent the shaped fixed core member from having a substantial effect on the overall shape of the distal tip of the guidewire 14. However, as shown by FIGS. 3 and 4, when the movable core 31 is extended axially in the proximal direction, the fixed core 33 assumes its preshaped state. Preferably, the fixed core 33 has a double curvature shape, with the most distal curved section 42 having a substantially smaller radius of curvature than the second curved section 43.

As shown in FIGS. 1 and 4, the double curvature of the fixed core member 33 is preferred in order to prevent traumatic engagement with the interior of the ventricle 12 of the heart 13 after the guidewire passes through the aortic valve 24.

When the guidewire is advanced through a stenotic valve, the distal portion of the movable core member 31 is generally coextensive with the preshaped fixed core member to provide increased pushability to the, guidewire to ensure passage across stenotic valve 24. However, once through the heart valve 24, the movable core 31 is axially moved in the proximal direction to allow the preshaped fixed core 33 to assume the double curvature shape. The smaller, more distal curvature 42 prevents the distal tip of the guidewire 14 from engaging the wall of the left ventricle 12. Further advancement of the guidewire toward the wall and further proximal movement of the movable core 31 urges the larger curved section 43 against the wall of the ventricular chamber, as shown in FIG. 1. This configuration also provides support to the portion of guidewire 14 which extends through the valve 24 to facilitate the advancing of the dilatation catheters 15, 16, and 17 over the guidewire 14 so that balloons 21, 22, and 23 thereof cross through the heart valve 24. Inflation of these balloons to relatively high pressures dilate the valve opening and thereby allow a greater amount of blood flow therethrough.

The diameter of the movable core 31 can vary from about 0.018 to about 0.035 inch (0.46–0.89 mm) at the proximal end to about 0.007 to about 0.015 of an inch (0.18–0.38 mm) at the distal end. Overall length can range from about 130 to 160 cm. The overall length of the tapered section 40 thereof ranges from about 15 to 25 cm. The diameter of the proximal end of the fixed core 33 can range from about 0.006 to about 0.012 inch (0.15–0.30 mm), the mid-section from about 0.007 to about 0.015 inch (0.03–0.38 mm) and the distal end a flattened section of about 0.001 to about 0.007 inch (0.025–0.10 mm) in thickness. The length of the fixed core 33 ranges from about 8 to about 20 cm.

While the present invention has been described herein in terms of dilating an aortic valve, the guidewire can also be used in mitral valve valvuloplasty. However, in mitral valve commissurotomy a transeptal approach is used wherein the guidewire and subsequently the dilatation catheters are percutaneously introduced into the patient's vasculature through the femoral vein and advanced into the right atrium. A small opening is made in the interatrial septum to pass the guidewire and subsequently the dilatation catheters into the left atrium and then advance the guidewire and catheters across the mitral valve. Usually the guidewire is further advanced through the aortic valve into the aorta. The valvuloplasty catheters are advanced across the guidewire to cross the mitral valve, the balloons thereof inflated to dilate the valve and then removed to facilitate blood flow therethrough. Further details of mitral valve commissurotomy can be found in R. G. McKay et al. *J. American College of Cardiology*, Vol. 7, No. 6, June 1986. See also J. E. Locka et al., *New England Journal of Medicine*, Vol. 313, pp 1515–81, 1985. Both of the above references are incorporated herein by reference.

The guidewire assembly of the invention can be utilized in a wide variety of vascular procedures in addition to valvuloplasty. Moreover, while the present invention has been described herein in terms of presently preferred embodiments, modifications can be made in the invention. For example, the outer tubular member has been described as a helical coil extended over a substantial part of the length thereof. Part or all of the coil can be replaced with a relatively thick walled flexible plastic tubular member. Other modifications and improvements can be made to the present invention without departing from the scope thereof.

What is claimed is:

1. A guidewire for guiding a catheter through a patient's vasculature comprising:
   (a) a flexible outer tubular body which includes a tubular member having proximal and distal extremities and a helical coil which is secured to the distal extremity of the tubular member and which has a rounded plug on the distal end thereof;
   (b) a first core member which is disposed within the outer tubular body and which is secured therein by the proximal end thereof to the distal extremity of the tubular member, said first core member having a preshaped set;
   (c) a second core member having greater stiffness than the first core member which is disposed within and which extends along essentially the entire length of the outer tubular body and which is axially movable therein; and
   (d) means at the proximal end of the second core member to facilitate the proximal movement of the second core member with respect to the first core member to allow the first core member to assume the preshaped set provided thereto.

2. The guidewire of claim 1 wherein the distal end of the first core member is secured to the plug at the distal end of the helical coil.

3. The guidewire of claim 1 wherein the tubular member includes a coil which extends over a substantial portion of the length thereof.

4. The guidewire of claim 3 wherein a helical coil is snugly wrapped about the tubular member.

5. The guidewire of claim 4 wherein the tubular member is formed of polyimide.

6. The guidewire of claim 1 wherein the first core member is provided with a preshaped set before the guidewire is introduced into a patient's vasculature.

7. The guidewire of claim 6 wherein the preshaped set of the first core member has two curved sections.

8. The guidewire of claim 7 wherein the most distal curved section has a smaller radius of curvature than the more proximal curved section.

9. The guidewire of claim 1 wherein the proximal end of the first core member is secured to a short intermediate tubular member which is secured to the distal extremity of the tubular member forming the outer tubular body.

10. A method of dilating a heart valve comprising:
    (a) advancing a guidewire through a patient's vasculature comprising a flexible outer tubular body which includes a tubular member with proximal and distal extremities and a helical coil secured by the proximal end thereof to the distal extremity of the tubular member having a rounded plug on the distal end thereof, a first core member having a preshaped set which is disposed within the tubular body and secured therein by the proximal end thereof to the distal extremity of the tubular member, a second core member having greater stiffness than the first core member which is disposed within and extends along essentially the entire length of the outer tubular body and is axially movable therein, and a means on the proximal end of the second core member to facilitate the proximal movement of the second core member with respect to the first core member;
    (b) positioning the second core member coextensive within the outer tubular member with the first core member so as to overcome the set of the first core member;
    (c) pushing the distal end of the guidewire through a stenotic heart valve;
    (d) after the distal portion of the guidewire has passed through the stenotic heart valve, axially moving the relatively stiff second core member in the proximal direction within the outer tubular member so the distal portion of the guidewire which has passed through the heart valve can assume the shape imposed by the preshaped first core member;
    (e) advancing at least one dilatation catheter having an inflatable balloon on the distal end thereof along the guidewire through the stenotic valve; and
    (f) inflating the inflatable balloon on the catheter to dilate the stenotic valve.

11. The method of claim 10 wherein the first core member is preshaped to have two curved sections.

12. The method claim 11 wherein the most distal curved section has a radius of curvature much less than the radius of curvature of the proximal curved section.

13. The method of claim 12 wherein the radius of curvature of the proximal curved section is at least five times larger than the radius of curvature of the distal curved section.

14. The method of claim 10 wherein the heart valve is the aortic valve, and the guidewire is percutaneously introduced into the femoral artery, advanced through the aortic arch and then through the aortic valve into the left ventricle.

15. The method of claim 14 wherein the second curved section of the guidewire is urged against the inner surface of the left ventricle to provide support for the guidewire.

16. The method of claim 10 wherein the heart valve is the mitral valve, and the guidewire is percutaneously introduced into the femoral vein, advanced through the right atrium, through an opening previously made in the interatrial septum into the left atrium and then through the mitral valve.

17. A method for performing a cardiovascular procedure, comprising:
    (a) advancing through a patient's vasculature a guidewire comprising a flexible outer tubular body which includes a tubular member with proximal and distal extremities and a helical coil secured by the proximal end thereof to the distal extremity of the tubular member and having a rounded plug on the distal end thereof, a first core member having a preshaped set which is disposed within the tubular body and being secured by the proximal end thereof to the distal end of the tubular member, a second core member having greater stiffness than the first core member which is disposed within and extends along essentially the entire length of the outer tubular body and is axially movable therein and a means on the proximal end of the second core member to facilitate the axial movement of the second core member with respect to the first core member within the outer tubular member;

(b) axially moving the relatively stiff second core member in the proximal direction within the outer tubular member so the distal portion of the guidewire can assume the shape imposed by the pre-shaped set of the first core member;

(c) advancing a vascular catheter along the guidewire to a desired location within the patient's vasculature;

(d) performing a vascular procedure with the catheter; and (e) removing the catheter and guidewire from the patient's vasculature.

* * * * *